United States Patent
Erkens et al.

(10) Patent No.: US 9,943,476 B2
(45) Date of Patent: *Apr. 17, 2018

(54) FOAMING BLEACH-BLONDING COMPOSITIONS

(71) Applicant: Henkel AG & Co. KGaA, Duesseldorf (DE)

(72) Inventors: Udo Erkens, Neuss-Grimlinghausen (DE); Burkhard Mueller, Duesseldorf (DE)

(73) Assignee: Henkel AG & Co. KGaA (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/045,385

(22) Filed: Feb. 17, 2016

(65) Prior Publication Data
US 2016/0158141 A1    Jun. 9, 2016

Related U.S. Application Data

(63) Continuation of application No. PCT/DE2014/200329, filed on Jul. 17, 2014.

(30) Foreign Application Priority Data

Aug. 28, 2013 (DE) ........................ 10 2013 217 207

(51) Int. Cl.
| | | |
|---|---|---|
| *A61Q 5/08* | (2006.01) | |
| *A61K 8/81* | (2006.01) | |
| *A61K 8/31* | (2006.01) | |
| *A61K 8/37* | (2006.01) | |
| *A61K 8/23* | (2006.01) | |
| *A61K 8/92* | (2006.01) | |

(52) U.S. Cl.
CPC .............. *A61K 8/8111* (2013.01); *A61K 8/23* (2013.01); *A61K 8/31* (2013.01); *A61K 8/37* (2013.01); *A61K 8/8117* (2013.01); *A61K 8/92* (2013.01); *A61Q 5/08* (2013.01)

(58) Field of Classification Search
None
See application file for complete search history.

(56) References Cited

U.S. PATENT DOCUMENTS

| 6,365,136 B1 | 4/2002 | Lauscher et al. |
| 7,803,355 B2 | 9/2010 | Legrand |
| 8,034,127 B2 * | 10/2011 | Bureiko .................. A61K 8/26 8/107 |
| 2011/0038818 A1 * | 2/2011 | Onyebuagu ............ A61K 8/042 424/62 |

FOREIGN PATENT DOCUMENTS

| EP | 1430875 A1 | 6/2004 |
| WO | 2005/072689 A1 | 8/2005 |
| WO | 2009/134875 A2 | 11/2009 |

OTHER PUBLICATIONS

Versagel M-seriesm Gelled Mineral Oil-All grades, Material Data Safety Sheet, Date of Issue Dec. 21, 2005.*
EWG's Skin Deep Cosmetic Database, C12-15 alkyl benzoate, accessed online Dec. 11, 2016.*
Hardyal, Sari, About Paraffin Oils, Aug. 16, 2013.*
PCT International Search Report (PCT/DE2014/200329) dated Oct. 20, 2014.

* cited by examiner

*Primary Examiner* — Robert A Wax
*Assistant Examiner* — Melissa S Mercier
(74) *Attorney, Agent, or Firm* — P. Scott Smith

(57) ABSTRACT

Agents for lightening keratinic fibers, which include, based on their weight, 20 to 75% by weight of oil(s), 0.05 to 5% by weight of polymer(s) from the group of ethylene/propylene/styrene copolymers and/or butylene/ethylene/styrene copolymers and/or butylene/propylene/styrene copolymers, and 1 to 70% by weight of peroxydisulfate(s), whereby the weight ratio of sodium peroxydisulfate in the agent to the total amount of peroxydisulfates in the agent is at least 0.2, possess increased storage stability, the improvement being not only in physical stability (sedimentation, phase separation) but also in chemical stability (degradation of the persalts). There are also improvements in product yield, spreadability of the application mixture, and the bleaching effect.

13 Claims, No Drawings

FOAMING BLEACH-BLONDING COMPOSITIONS

FIELD OF THE INVENTION

The present invention generally relates to agents for oxidative color changing in the field of cosmetics, which are suitable in particular for lightening keratinic fibers, particularly human hair.

BACKGROUND OF THE INVENTION

The oxidizing agents present in bleaching agents are capable of lightening hair fiber by the oxidative breakdown of the hair's own pigment, melanin. For a moderate bleaching effect, the use of hydrogen peroxide as the sole oxidizing agent is sufficient, optionally with the use of ammonia or other alkalizing agents; a mixture of hydrogen peroxide and peroxydisulfate salts and/or peroxymonosulfate salts is typically used to achieve a greater bleaching effect.

For reasons of stability, commercial bleaching agents are customarily offered in two preparations packaged separate from one another, which are mixed immediately before use to form a finished application preparation. Commercial bleaching agents typically consist of a liquid oxidizing agent preparation and a powder including solid oxidizing agents. Alternatively, instead of the powder, pasty agents can be mixed with a liquid oxidizing agent preparation, as a result of which the problem of dust during the production and during mixing is prevented. Products with other components are also offered commercially.

Pasty bleaching agents usually include higher amounts of an inert oil, which can lead to stability problems (sedimentation of the solid oxidizing agents out of the oil). Even with peroxydisulfates that have not sedimented completely, a concentration gradient can occur within the packaging, so that different portions from the packaging after being mixed can produce a different lightening effect. A high viscosity is desirable to minimize these problems.

On the other hand, the viscosity of the bleaching paste must be so low that it can be mixed well and rapidly with the liquid oxidizing agent preparation. The resulting bleaching mixture must be sufficiently liquid, moreover, in order to the applied easily and uniformly, but viscous enough in order not to drip off the head or from application aids such as brushes. In addition, the resulting bleaching mixture should not separate, because sedimentation or phase separation is perceived by customers as a quality defect.

WO 2009/134875 A1 describes bleaching agents including persulfate salts and an oil gel, which in turn consists of oil(s) and specific polymers.

According to this invention, stability with respect to sedimentation and phase separation are cited as desirable properties of the agent.

EP 1 034 777 A1 discloses agents for lightening keratinic fibers, which include at least two preparations (A) and (B) packaged separate from one another, which are mixed immediately before use to form an application mixture, whereby preparations (A) are oil-based and include polymer(s), which form oelogels or lipogels.

The bleaching pastes disclosed in the state of the art are notable for low foaming of the application mixture. It has now been found that because of the rather large surface area of the application mixture, foaming can be quite desirable, because the product yield, spreadability of the application mixture, and the bleaching effect can be improved.

It is therefore desirable to improve further the properties of bleaching agents; in this case, on the one hand, the storage stability is to be increased, whereby not only the physical stability (sedimentation, phase separation) but also the chemical stability (decomposition of the persalts) are to be improved. Moreover, in particular the product yield, distributability of the application mixture, and the bleaching effect should be improved.

Furthermore, other desirable features and characteristics of the present invention will become apparent from the subsequent detailed description of the invention and the appended claims, taken in conjunction with the accompanying drawings and this

BRIEF SUMMARY OF THE INVENTION

An agent for lightning keratinic fibers includes, based on its weight, 20 to 75% by weight of oil(s); 0.05 to 5% by weight of polymer(s) from the group of copolymers of ethylene/propylene/styrene, copolymers of butylene/ethylene/styrene, copolymers of butylene/propylene/styrene; and 1 to 70% by weight of peroxydisulfate(s), wherein the weight ratio of sodium peroxydisulfate in the agent to the total amount of peroxydisulfates in the agent is at least 0.2.

A method for changing the color of keratinic fibers includes mixing two preparations (A) and (B), originally packaged separate from one another, of which preparation (A) includes at least one persulfate and preparation (B) at least one oxidizing agent, to form an application mixture. The mixture is applied to the fibers and rinsed out again after a treatment time. Preparation (A) includes 20 to 75% by weight of oil(s); 0.05 to 5% by weight of polymer(s) from the group including copolymers of ethylene/propylene/styrene, copolymers of butylene/ethylene/styrene, copolymers of butylene/propylene/styrene; and 1 to 70% by weight of peroxydisulfate(s). The weight ratio of sodium peroxydisulfate in the agent to the total amount of peroxydisulfates in the agent is at least 0.2.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

The present invention is based on the finding that bleaching pastes, which have a higher oil content and are thickened with special polymers, are especially stable and effectively foamable or self-foaming with the indicated advantages when the employed persulfates meet certain criteria.

The subject matter of the present invention in a first embodiment is agents for lightening keratinic fibers, including, based on their weight,
  a) 20 to 75% by weight of oil(s);
  b) 0.05 to 5% by weight of polymer(s) from the group including
   i. copolymers of ethylene/propylene/styrene,
   ii. copolymers of butylene/ethylene/styrene,
   iii. copolymers of butylene/propylene/styrene,
  c) 1 to 70% by weight of peroxydisulfate(s),
wherein the weight ratio of sodium peroxydisulfate in the agent to the total amount of peroxydisulfates in the agent is at least 0.2.

Keratinic fibers or keratin fibers as well are to be understood to mean pelts, wool, feathers, and in particular human hair. Although the agents of the invention are primarily suitable for lightening keratin fibers, in principle nothing precludes use in other fields as well.

The agents of the invention include as a first ingredient one or more oil(s). Preferably, these oil(s) are liquid under normal conditions.

In the case of cosmetic oils, a distinction is made between volatile and non-volatile oils. Non-volatile oils are understood to mean oils that at 20° C. and an ambient pressure of 1013 hPa have a vapor pressure of less than 2.66 Pa (0.02 mm Hg). Volatile oils are understood to mean oils that at 20° C. and an ambient pressure of 1013 hPa have a vapor pressure of 2.66 Pa to 40,000 Pa (0.02 mm to 300 mm Hg), preferably 10 to 12,000 Pa (0.1 to 90 mm Hg), especially preferably 13 to 3000 Pa, and exceedingly preferably 15 to 500 Pa.

Volatile cosmetic oils are typically selected from among cyclic silicone oils with the INCI name Cyclomethicone. Understood under the INCI name Cyclomethicone are particularly cyclotrisiloxane (hexamethylcyclotrisiloxane), cyclotetrasiloxane (octamethylcyclotetrasiloxane), cyclopentasiloxane (decamethylcyclopentasiloxane), and cyclohexasiloxane (dodecamethylcyclohexasiloxane). These oils at 20° C. have a vapor pressure of about 13 to 15 Pa.

A cyclomethicone substitute preferred according to the invention is a mixture of $C_{13}$-$C_{16}$ isoparaffins, $C_{12}$-$C_{14}$ isoparaffins, and $C_{13}$-$C_{15}$ alkanes, whose viscosity at 25° C. is in the range of 2 to 6 mPas and which has a vapor pressure at 20° C. in the range of 10 to 150 Pa, preferably 100 to 150 Pa. Such a mixture can be obtained, e.g., under the name: SiClone SR-5 from the company Presperse Inc.

Other preferred volatile silicone oils are selected from volatile linear silicone oils, particularly volatile linear silicone oils with 2 to 10 siloxane units, such as hexamethyldisiloxane ($L_2$), octamethyltrisiloxane ($L_3$), and decamethyltetrasiloxane ($L_4$), as they are present, e.g., in the commercial products DC 21184, Dow Corning® 200 (0.65 cSt), and Dow Corning® 200 (1.5 cSt) from Dow Corning, and low-molecular-weight phenyl trimethicones with a vapor pressure of about 2000 Pa at 20° C., as can be obtained, for example, from GE Bayer Silicones/Momentive under the name Baysilone Fluid PD 5.

Other preferred products of the invention include at least one volatile non-silicone oil. Preferred volatile non-silicone oils are selected from $C_8$-$C_{16}$ isoparaffins, particularly from isononane, isodecane, isoundecane, isododecane, isotridecane, isotetradecane, isopentadecane, and isohexadecane, and mixtures thereof. Preferred are $C_{10}$-$C_{13}$ isoparaffin mixtures, particularly those with a vapor pressure at 20° C. of 10 to 400 Pa, preferably 13 to 100 Pa.

Especially preferred further as a cosmetic oil according to the invention are esters of linear or branched, saturated or unsaturated fatty alcohols having 2 to 30 carbon atoms with linear or branched, saturated or unsaturated fatty acids having 2 to 30 carbon atoms, which can be hydroxylated. Preferred are esters of linear or branched, saturated fatty alcohols having 2 to 5 carbon atoms with linear or branched, saturated or unsaturated fatty acids having 10 to 18 carbon atoms, which may be hydroxylated. Preferred examples of these are isopropyl palmitate, isopropyl stearate, isopropyl myristate, 2-hexyldecyl stearate, 2-hexyldecyl laurate, isodecyl neopentanoate, isononyl isononanoate, 2-ethylhexyl palmitate, and 2-ethylhexyl stearate. Likewise preferred are isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid-2-butyloctanoate, diisotridecyl acetate, n-butyl stearate, n-hexyl laurate, n-decyl oleate, oleyl oleate, oleyl erucate, erucyl oleate, erucyl erucate, ethylene glycol dioleate, ethylene glycol dipalmitate, n-hexyl laurate, n-decyl oeleat, oleyl oleate, oleyl erucate, erucyl oleate, $C_{12}$-$C_{15}$ alkyl lactate, and di-$C_{12}$-$C_{13}$-alkyl malate, and the benzoic acid esters of linear or branched $C_{8-22}$ alkanols. Especially preferred are benzoic acid-$C_{12}$-$C_{15}$-alkyl esters, e.g., obtainable as the commercial product Finsolv® TN ($C_{12}$-$C_{15}$ alkyl benzoate), and benzoic acid isostearyl esters, e.g., obtainable as Finsolv® SB, 2-ethylhexyl benzoate, e.g., obtainable as Finsolv® EB, and benzoic acid-2-octyldodecyl esters, e.g., obtainable as Finsolv® BOD.

Especially preferred further as a cosmetic oil according to the invention are esters of linear or branched, saturated or unsaturated fatty alcohols having 2 to 30 carbon atoms with linear or branched, saturated or unsaturated fatty acids having 2 to 30 carbon atoms, which can be hydroxylated. Preferred are esters of linear or branched, saturated fatty alcohols having 2 to 5 carbon atoms with linear or branched, saturated or unsaturated fatty acids having 10 to 18 carbon atoms, which may be hydroxylated. Preferred examples of these are isopropyl palmitate, isopropyl stearate, isopropyl myristate, 2-hexyldecyl stearate, 2-hexyldecyl laurate, isodecyl neopentanoate, isononyl isononanoate, 2-ethylhexyl palmitate, and 2-ethylhexyl stearate. Likewise preferred are isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid-2-butyloctanoate, diisotridecyl acetate, n-butyl stearate, n-hexyl laurate, n-decyl oleate, oleyl oleate, oleyl erucate, erucyl oleate, erucyl erucate, ethylene glycol dioleate, ethylene glycol dipalmitate, n-hexyl laurate, n-decyl oeleat, oleyl oleate, oleyl erucate, erucyl oleate, $C_{12}$-$C_{15}$ alkyl lactate, and di-$C_{12}$-$C_{13}$-alkyl malate, and the benzoic acid esters of linear or branched $C_{8-22}$ alkanols. Especially preferred are benzoic acid-$C_{12}$-$C_{15}$-alkyl esters, e.g., obtainable as the commercial product Finsolv® TN ($C_{12}$-$C_{15}$ alkyl benzoate), and benzoic acid isostearyl esters, e.g., obtainable as Finsolv® SB, 2-ethylhexyl benzoate, e.g., obtainable as Finsoly® EB, and benzoic acid-2-octyldodecyl esters, e.g., obtainable as Finsolv® BOD.

Especially preferred further as a cosmetic oil according to the invention are esters of linear or branched, saturated or unsaturated fatty alcohols having 2 to 30 carbon atoms with linear or branched, saturated or unsaturated fatty acids having 2 to 30 carbon atoms, which can be hydroxylated. Preferred are esters of linear or branched, saturated fatty alcohols having 2 to 5 carbon atoms with linear or branched, saturated or unsaturated fatty acids having 10 to 18 carbon atoms, which may be hydroxylated. Preferred examples of these are isopropyl palmitate, isopropyl stearate, isopropyl myristate, 2-hexyldecyl stearate, 2-hexyldecyl laurate, isodecyl neopentanoate, isononyl isononanoate, 2-ethylhexyl palmitate, and 2-ethylhexyl stearate. Likewise preferred are isopropyl isostearate, isopropyl oleate, isooctyl stearate, isononyl stearate, isocetyl stearate, isononyl isononanoate, isotridecyl isononanoate, cetearyl isononanoate, 2-ethylhexyl laurate, 2-ethylhexyl isostearate, 2-ethylhexyl cocoate, 2-octyldodecyl palmitate, butyloctanoic acid-2-butyloctanoate, diisotridecyl acetate, n-butyl stearate, n-hexyl laurate, n-decyl oleate, oleyl oleate, oleyl erucate, erucyl oleate, erucyl erucate, ethylene glycol dioleate, ethylene glycol dipalmitate, n-hexyl laurate, n-decyl oeleat, oleyl oleate, oleyl erucate, erucyl oleate, $C_{12}$-$C_{15}$ alkyl lactate, and di-$C_{12}$-$C_{13}$-alkyl malate, and the benzoic acid esters of linear or branched $C_{8-22}$ alkanols. Especially preferred are benzoic acid-$C_{12}$-$C_{15}$-alkyl esters, e.g., obtainable as the commercial product Finsolv® TN ($C_{12}$-$C_{15}$ alkyl benzoate), and benzoic acid isostearyl esters, e.g., obtainable as Finsolv® SB, 2-ethylhexyl benzoate, e.g., obtainable as Finsolv® EB, and benzoic acid-2-octyldodecyl esters, e.g., obtainable as Finsolv® BOD.

The term "triglycerides" used hereafter refers to "glycerol triesters." Other nonvolatile oils preferred according to the invention are selected from the triglycerides of linear or branched, saturated or unsaturated, optionally hydroxylated $C_{8-30}$ fatty acids, provided these are liquid under normal conditions. The use of natural oils, e.g., soybean oil, cottonseed oil, sunflower oil, palm oil, palm kernel oil, linseed oil, almond oil, castor oil, corn oil, rapeseed oil, olive oil, sesame oil, thistle oil, wheat germ oil, peach kernel oil, and the liquid fractions of coconut oil, and the like can be especially suitable. Especially preferred are synthetic triglycerides, particularly capric/caprylic triglycerides, e.g., the commercial products Myritol® 318 or Myritol® 331 (BASF/Cognis) with unbranched fatty acid esters, as well as glyceryl triisostearin and glyceryl tri(2-ethylhexanoate) with branched fatty acid esters. Such triglyceride oils preferably constitute a fraction of less than 50% by weight of the total weight of all cosmetic oils in the product of the invention. Other nonvolatile non-silicone oils especially preferred according to the invention are selected from dicarboxylic acid esters of linear or branched $C_2$-$C_{10}$ alkanols, particularly diisopropyl adipate, di-n-butyl adipate, di-(2-ethylhexyl) adipate, dioctyl adipate, diethyl/di-n-butyl/dioctyl sebacate, diisopropyl sebacate, dioctyl malate, dioctyl maleate, dicaprylyl maleate, diisooctyl succinate, di-2-ethylhexyl succinate, and di-(2-hexyldecyl) succinate.

Other nonvolatile non-silicone oils especially preferred according to the invention are selected from the symmetric, asymmetric, or cyclic esters of carbonic acid with $C_6$-$C_{20}$ alcohols, e.g., di-n-caprylyl carbonate (Cetiol® CC) or di-(2-ethylhexyl) carbonate (Tegosoft DEC). Esters of carbonic acid with $C_1$-$C_5$ alcohols, e.g., glycerol carbonate or propylene carbonate, in contrast, are not compounds that are suitable as cosmetic oils.

Other oils, which may be preferred according to the invention, are selected from the esters of dimers of unsaturated $C_{12}$-$C_{22}$ fatty acids (dimer fatty acids) with monohydric linear, branched, or cyclic $C_2$-$C_{18}$ alkanols or with polyhydric linear or branched $C_2$-$C_6$ alkanols. Especially preferably, the total weight of dimer fatty acid esters is 0.5 to 10% by weight, preferably 1 to 5% by weight, based in each case on the weight of the total water-in-oil emulsion, without the weight of the propellant being considered.

Other cosmetic oils, especially preferred according to the invention, are selected from nonvolatile silicone oils. Nonvolatile silicone oils preferred according to the invention are selected from linear polyalkylsiloxanes with a kinematic viscosity at 25° C. of at least 5 cSt to 2000 cSt, particularly selected from linear polydimethylsiloxanes with a kinematic viscosity at 25° C. of 5 cSt to 2000 cSt, preferably 10 to 350 cSt, especially preferably 50 to 100 cSt, as can be obtained, e.g., under the trade name Dow Corning® 200 or Xiameter PMX from Dow Corning or Xiameter. Other preferred nonvolatile silicone oils are phenyltrimethicones with a kinematic viscosity at 25° C. of 10 to 100 cSt, preferably of 15 to 30 cSt, and cetyl dimethicones.

Agents preferred according to the invention include at least one nonvolatile silicone oil, which is preferably selected from linear polyalkylsiloxanes with a kinematic viscosity at 25° C. of 5 cSt to 2000 cSt, preferably 10 to 350 cSt, especially preferably 50 to 100 cSt, particularly selected from linear polydimethylsiloxanes with a kinematic viscosity at 25° C. of 5 cSt to 2000 cSt, preferably 10 to 350 cSt, especially preferably 50 to 100 cSt, in a total amount of 0.1 to 30% by weight, preferably 1 to 24% by weight, especially preferably 2 to 18% by weight, exceedingly preferably 4 to 10% by weight, based in each case on the weight of the total agent.

Some of the mentioned oils have proven to be especially suitable, because they guarantee the physical and chemical stability of the bleaching agent pastes over long time periods and are greatly compatible with the other ingredients of the invention. Agents preferred according to the invention are characterized in that they include 22.5 to 70% by weight, preferably 25 to 65% by weight, more preferably 27.5 to 60% by weight, especially preferably 30 to 55% by weight, and particularly 32.5 to 50% by weight of oil(s) from the group including paraffin oil, polyisobutene, alkyl benzoates, isopropyl palmitate, isohexadecane, isododecane, and isononyl-isononanoate.

Other preferred agents of the invention include 20 to 60% by weight, preferably 22.5 to 55% by weight, more preferably 25 to 50% by weight, especially preferably 27.5 to 45% by weight, and particularly 30 to 40% by weight of paraffin oil.

The agents of the invention include as another ingredient 0.05 to 5% by weight of polymer(s) from the group of copolymers of ethylene/propylene/styrene, and/or copolymers of butylene/ethylene/styrene, and/or copolymers of butylene/propylene/styrene.

Preferably, the mentioned copolymers are not copolymers in which the monomer units are randomly distributed but block copolymers, especially preferably diblock copolymers or triblock copolymers. Such block copolymers then have "hard" segments of polystyrene and "soft" segments of ethylene/propylene or ethylene/butylene or propylene/butylene. The individual blocks in this case can include 10 to 10,000, preferably 50 to 5000, and particularly 100 to 500 monomers. Preferred diblock copolymers are styrene-ethylene/propylene (S-EP) and styrene-ethylene/butylene (S-EB); preferred triblock copolymers are styrene-ethylene/propylene-styrene (S-EP-S) and styrene-ethylene/butylene-styrene (S-EB-S). Especially preferred according to the invention is the use of mixtures of diblock and triblock copolymers, whereby mixtures of styrene-ethylene/propylene (S-EP) and styrene-ethylene/propylene-styrene (S-EP-S) have proven to be especially preferable. Very especially preferably, in this case, the proportion of diblock copolymers is 10 to 90% by weight and the proportion of triblock copolymers 90 to 10% by weight, based in each case on the weight of the polymer mixture.

Agents preferred according to the invention are characterized in that they include 0.1 to 4% by weight, preferably 0.15 to 3% by weight, more preferably 0.2 to 2.5% by weight, especially preferably 0.25 to 2% by weight, more preferably 0.3 to 1.5% by weight, and particularly 0.35 to 0.75% by weight of ethylene/propylene/styrene copolymers.

Agents especially preferred according to the invention are characterized in that they include 0.1 to 4% by weight, preferably 0.15 to 3% by weight, more preferably 0.2 to 2.5% by weight, especially preferably 0.25 to 2% by weight, more preferably 0.3 to 1.5% by weight, and particularly 0.35 to 0.75% by weight of diblock copolymers of ethylene/propylene/styrene (S -EP).

Agents likewise especially preferred according to the invention are characterized in that they include 0.1 to 4% by weight, preferably 0.15 to 3% by weight, more preferably 0.2 to 2.5% by weight, especially preferably 0.25 to 2% by weight, more preferably 0.3 to 1.5% by weight, and particularly 0.35 to 0.75% by weight of triblock copolymers of ethylene/propylene/styrene (S-EP-S).

Especially preferred diblock copolymers of ethylene/propylene/styrene (S-EP) can be described by the formula (I)

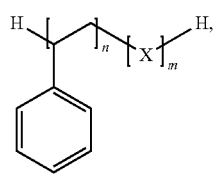

(I)

where —[X]$_m$— stands for a block, which has ethylene and propylene monomer units, which can be present distributed as a block or randomly, whereby m stands for a number from 10 to 10,000, preferably from 50 to 5000, and particularly from 100 to 500 and refers to the total number of ethylene and propylene monomer units in the block, and n stands for a number from 10 to 10,000, preferably from 50 to 5000, and particularly from 100 to 500.

Especially preferred triblock copolymers of ethylene/propylene/styrene (S-EP-S) can be described by the formula (II)

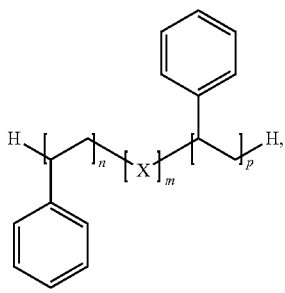

(II)

where —[X]$_m$— stands for a block, which has ethylene and propylene monomer units, which can be present distributed as a block or randomly, whereby m stands for a number from 10 to 10,000, preferably from 50 to 5000, and particularly from 100 to 500 and refers to the total number of ethylene and propylene monomer units in the block, and n and p independently of one another stand for a number from 10 to 10,000, preferably from 50 to 5000, and particularly from 100 to 500.

Agents preferred according to the invention are characterized in that they include 0.1 to 4% by weight, preferably 0.15 to 3% by weight, more preferably 0.2 to 2.5% by weight, especially preferably 0.25 to 2% by weight, more preferably 0.3 to 1.5% by weight, and particularly 0.35 to 0.75% by weight of butylene/ethylene/styrene copolymers.

Agents likewise especially preferred according to the invention are characterized in that they include 0.1 to 4% by weight, preferably 0.15 to 3% by weight, more preferably 0.2 to 2.5% by weight, especially preferably 0.25 to 2% by weight, more preferably 0.3 to 1.5% by weight, and particularly 0.35 to 0.75% by weight of diblock copolymers of butylene/ethylene/styrene (S-EB).

Agents likewise especially preferred according to the invention are characterized in that they include 0.1 to 4% by weight, preferably 0.15 to 3% by weight, more preferably 0.2 to 2.5% by weight, especially preferably 0.25 to 2% by weight, more preferably 0.3 to 1.5% by weight, and particularly 0.35 to 0.75% by weight of triblock copolymers of butylene/ethylene/styrene (S-EB-S).

Especially preferred diblock copolymers of butylene/ethylene/styrene, (S-EB) can be described by the formula (III)

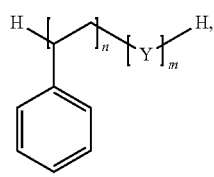

(III)

where —[Y]$_m$— stands for a block, which has ethylene and butylene monomer units, which can be present distributed as a block or randomly, whereby m stands for a number from 10 to 10,000, preferably from 50 to 5000, and particularly from 100 to 500 and refers to the total number of ethylene and butylene monomer units in the block, and n stands for a number from 10 to 10,000, preferably from 50 to 5000, and particularly from 100 to 500.

Especially preferred triblock copolymers of butylene/ethylene/styrene (S-EB-S) can be described by the formula (IV)

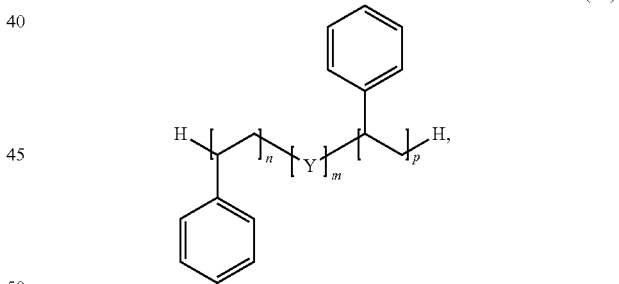

(IV)

where —[Y]$_m$— stands for a block, which has ethylene and butylene monomer units, which can be present distributed as a block or randomly, whereby m stands for a number from 10 to 10,000, preferably from 50 to 5000, and particularly from 100 to 500 and refers to the total number of ethylene and butylene monomer units in the block, and n and p independently of one another stand for a number from 10 to 10,000, preferably from 50 to 5000, and particularly from 100 to 500.

The preparations of the invention include as another essential ingredient 1 to 70% by weight of peroxydisulfate(s), whereby the weight ratio of sodium peroxydisulfate present in the agent to the total amount of peroxydisulfates present in the agent is at least 0.2. This weight ratio is determined in that the percentage by weight amount of sodium peroxydisulfate is divided by the sum of the percentage by weight amounts of all peroxydisulfates. In other words, at least 20% sodium peroxydisulfate is present, based on the total amount of all peroxydisulfates.

Other agents preferred according to the invention are characterized in that the weight ratio of sodium peroxydisulfate in the agent to the total amount of peroxydisulfates in the agent is 0.2 to 0.5, preferably 0.21 to 0.475, more preferably 0.22 to 0.45, especially preferably 0.23 to 0.425, more preferably 0.25 to 0.4, and particularly 0.26 to 0.35. In other words, 20 to 50%, preferably 21 to 47.5%, more preferably 22 to 45%, especially preferably 23 to 42.5%, more preferably 25 to 40%, and particularly 26 to 35% of sodium peroxydisulfate, based on the total amount of all peroxydisulfates, are present in these preferred agents.

Based on the agents of the invention, agents are preferred that include 5 to 20% by weight, preferably 6 to 18% by weight, more preferably 7 to 16% by weight, especially preferably 8 to 14% by weight, and particularly 10 to 12% by weight of sodium peroxydisulfate.

Based on the agents of the invention, agents are preferred that include 5 to 20% by weight, preferably 6 to 18% by weight, more preferably 7 to 16% by weight, especially preferably 8 to 14% by weight, and particularly 10 to 12% by weight of sodium peroxydisulfate.

Ammonium peroxydisulfate, if it is used, is used preferably in the lower amounts. Based on the agents of the invention, agents are preferred that include 0 to <2.5% by weight, preferably 0 to <1% by weight, more preferably 0 to <0.5% by weight, especially preferably 0 to <0.1% by weight, and particularly 0% by weight of ammonium peroxydisulfate.

The agents of the invention can include at least one natural polymer as another ingredient. Cellulose derivatives, for example, which are used as thickening agents, can be used as the natural polymer. Examples are agar-agar, carrageenan, alginates, xanthan gum, karaya gum, gum ghatti, tragacanth, scleroglucan gums, or gum arabic, alginates, pectins, polyoses, guar gums, locust bean gum, flaxseed gums, dextrans, pectins, starch fractions, and derivatives such as amylose, amylopectin and dextrins, gelatin, and casein, as well as cellulose derivatives, such as, for example, methylcellulose, carboxyalkylcelluloses, such as carboxymethylcellulose, and hydroxyalkylcelluloses such as hydroxyethylcellulose.

Natural polymers from the mentioned substance classes are commercially available and are offered, for example, under the trade names Deuteron®-XG (anionic heteropolysaccharide based on β-D-glucose, D-mannose, D-glucuronic acid, Schoener GmbH), Deuteron®-XN (non-ionogenic polysaccharide, Schoener GmbH), Protanal RF 6650 alginate (sodium alginate, FMC Biopolymer), Cekol (cellulose gum, Kelco), Kelzan (xanthan biopolymer, Kelco), Xanthan FN (xanthan biopolymer, Jungbunzlauer), Keltrol, e.g., Keltrol CG-T (xanthan biopolymer, Kelco), or Keltrol CG-SFT (xanthan biopolymer, Kelco).

In a preferred embodiment of the invention, the agents of the invention include xanthan. Preferred according to the invention are xanthans that afford transparent preparations after swelling. Especially preferred is the use of the xanthan biopolymer, which is sold under the trade name Keltrol CG-SFT by the company Kelco.

In a preferred embodiment, an agent of the invention includes 0.1 to 5% by weight, preferably 0.5 to 4% by weight, more preferably 1 to 3% by weight, especially preferably 1.25 to 2.5% by weight, and particularly 1.5 to 2% by weight of xanthan.

The agents of the invention can include as consistency imparting agents preferably long-chain fatty alcohols, which are selected preferably from the group including arachidyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and brassidyl alcohol ((13E)-docosen-1-ol).

These long-chain fatty alcohols have a chain length of at least 20 C atoms. Within this group, special long-chain fatty alcohols have proven to be very especially suitable.

In an especially preferred embodiment, an agent for the bleaching of keratinic fibers is characterized in that it includes arachidyl alcohol (eicosan-1-ol).

In another especially preferred embodiment, an agent for the bleaching of keratinic fibers is characterized in that it includes behenyl alcohol (docosan-1-ol).

In another especially preferred embodiment, an agent for the bleaching of keratinic fibers is characterized in that it includes arachidyl alcohol (eicosan-1-ol) and/or behenyl alcohol (docosan-1-ol).

It has emerged, furthermore, that it is of advantage, if the long-chain fatty alcohols, particularly arachidyl alcohol (eicosan-1-ol) and/or behenyl alcohol (docosan-1-ol), are present in specific amount ranges in the agent of the invention. Preferred agents of the invention include one or more long-chain fatty alcohols (a) from the group including arachidyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and brassidyl alcohol ((13E)-docosen-1-ol) in a total amount of 0.3 to 3.4% by weight, preferably of 0.4 to 2.6% by weight, more preferably of 0.5 to 1.8% by weight, and especially preferably of 0.6 to 0.9% by weight, based on the total weight of the ready-to-use agent.

In a very especially preferred embodiment, an agent of the invention is characterized in that it includes as fatty alcohol(s) arachadyl alcohol (eicosan-1-ol) and/or behenyl alcohol (docosan-1-ol) in a total amount of 0.3 to 3.4% by weight, preferably of 0.4 to 2.6% by weight, more preferably of 0.5 to 1.8% by weight, and especially preferably of 0.6 to 0.9% by weight, based on the total weight of the ready-to-use agent.

Apart from the special long-chain fatty alcohols with a chain length of at least 20 C atoms, the agent of the invention can include in addition also still other, shorter-chain fatty alcohols with a chain length of 12 to 18 C atoms. Suitable shorter-chain fatty alcohols with a saturated $C_{12}$-$C_{18}$ alkyl chain are, for example, dodecan-1-ol (dodecyl alcohol, lauryl alcohol), tetradecan-1-ol (tetradecyl alcohol, myristyl alcohol), hexadecan-1-ol (hexadecyl alcohol, cetyl alcohol, palmityl alcohol), and octadecan-1-ol (octadecyl alcohol, stearyl alcohol). A suitable shorter-chain fatty alcohol with an unsaturated $C_{12}$-$C_{18}$ alkyl chain is, for example, (9Z)-octadec-9-en-1-ol (oleyl alcohol).

Very especially preferred in regard to the consistency of the products of the invention as well as to their ability to be applied is the use of branched longer-chain alcohols with a chain length of 12 to 18 C atoms, whereby hexyldecanol has proven to be especially suitable. Agents especially preferred according to the invention are characterized in that they contain, based on their weight, 2 to 10% by weight, more preferably 3.5 to 8% by weight, especially preferably 4 to 7% by weight, and particularly 5 to 6.5% by weight of branched longer-chain alcohols with a chain length of 12 to 18 C atoms, preferably 2-hexyldecan-1-ol.

Cetyl stearyl alcohol is especially suitable for physical and chemical stabilization. Agents of the invention are preferred here that include 1 to 15% by weight, preferably 2 to 10% by weight, more preferably 3.5 to 8% by weight, especially preferably 4 to 7% by weight, and particularly 5 to 6.5% by weight of cetearyl alcohol.

The bleaching agent can contain, furthermore, alkalizing agents. Preferred alkalizing agents are, for example, ammonia, alkanolamines, basic amino acids, and inorganic alkalizing agent such as alkali (alkaline earth) metal hydroxides, alkali (alkaline earth) metal metasilicates, alkali (alkaline earth) metal phosphates, and alkali (alkaline earth) metal hydrogen phosphates. Lithium, sodium, and/or potassium are used preferably as metal ions. Ammonia is an especially preferred alkalizing agent.

The inorganic alkalizing agents usable according to the invention are preferably selected from sodium hydroxide, potassium hydroxide, calcium hydroxide, barium hydroxide, sodium phosphate, potassium phosphate, sodium silicate, potassium silicate, magnesium silicate, sodium carbonate, and potassium carbonate. Sodium hydroxide and/or potassium hydroxide are especially preferred.

It has emerged as preferable to use metasilicates in the compositions of the invention. These increase the bleaching effect with simultaneously reduced damage to keratinic fibers. Preferably alkali (alkaline earth) metal metasilicates, especially preferably alkali metal metasilicates, and particularly sodium metasilicate have proven to be suitable. Agents preferred according to the invention, therefore, contain, based on their weight, 5 to <10% by weight, preferably 6 to <9.5% by weight, more preferably 6.5 to <9% by weight, especially preferably 7 to <8.5% by weight, and particularly 7.5 to <8% by weight of alkali (alkaline earth) metal metasilicates, preferably alkali metal metasilicates, and particularly sodium metasilicate.

Alkalizing agents that can be used according to the invention are preferably selected from alkanolamines of primary, secondary, or tertiary amines with a $C_2$-$C_6$ alkyl parent structure, bearing at least one hydroxyl group. Especially preferred alkanolamines are selected from the group, formed by 2-aminoethan-1-ol (monoethanolamine), 3-aminopropan-1-ol, 4-aminobutan-1-ol, 5-aminopentan-1-ol, 1-aminopropan-2-ol (monoisopropanolamine), 1-aminobutan-2-ol, 1-aminopentan-2-ol, 1-aminopentan-3-ol, 1-aminopentan-4-ol, 2-amino-2-methylpropanol, 2-amino-2-methylbutanol, 3-amino-2-methylpropan-1-ol, 1-amino-2-methylpropan-2-ol, 3-aminopropane-1,2-diol, 2-amino-2-methylpropane-1,3-diol, 2-amino-2-ethyl-1,3-propanediol, N,N-dimethylethanolamine, methylglucamine, triethanolamine, diethanolamine, and triisopropanolamine. Especially preferred alkanolamines are monoethanolamine, 2-amino-2-methylpropanol, and triethanolamine.

The basic amino acids that can be used as alkalizing agents of the invention are preferably selected from the group, formed by L-arginine, D-arginine, D/L-arginine, L-lysine, D-lysine, D/L-lysine, L-ornithine, D-ornithine, D/L-ornithine, L-histidine, D-histidine, and/or D/L-histidine. L-Arginine, D-arginine, and/or D/L-arginine are used especially preferably as an alkalizing agent within the meaning of the invention.

Many clients perceive the intense odor production by ammonia as irritating or annoying. Although ammonia is a preferred alkalizing agent, ready-to-use preparations can therefore be preferred according to the invention that are free of ammonia. Preferred alkalizing agents for preparations that are free of ammonia are monoethanolamine, 2-amino-2-methylpropanol, and triethanolamine.

If the ready-to-use mixtures include alkalizing agents, preparations are preferred according to the invention that include the alkalizing agents in an amount of 0.05 to 20% by weight, particularly of 0.5 to 10% by weight, based in each case on the total weight of the ready-to-use agent.

The compositions of the invention can include in addition at least one other bleach booster, which is different from the inorganic persalts.

Compounds that under perhydrolysis conditions afford aliphatic peroxycarboxylic acids having preferably 1 to 10 C atoms, especially 2 to 4 C atoms, and/or optionally substituted perbenzoic acid can be used as bleach boosters. Substances carrying 0-and/or N-acyl groups with said number of C atoms and/or optionally substituted benzoyl groups are suitable. Preferred are multiply acylated alkylene diamines, especially tetraacetylethylenediamine (TAED), acylated triazine derivatives, especially 1,5-diacetyl-2,4-dioxohexahydro-1,3,5-triazine (DADHT), acylated glycourils, especially tetraacetylglycouril (TAGU), N-acylimides, especially N-nonanoylsuccinimide (NOSI), acylated phenolsulfonates, especially n-nonanoyl- or isononanoyloxybenzenesulfonate (n- or iso-NOBS), carboxylic acid anhydrides, especially phthalic anhydride, acylated polyhydric alcohols, especially triacetin, ethylene glycol diacetate, and 2,5-diacetoxy-2,5-dihydrofuran.

A second subject matter of the invention is a method for changing the color of keratinic fibers, in which at least two preparations (A) and (B), packaged separate from one another, of which preparation (A) includes at least one persulfate and preparation (B) at least one oxidizing agent, are mixed to form an application mixture, and said mixture is applied to fibers and is rinsed out again after a treatment time, characterized in that preparation (A) includes
  a) 20 to 75% by weight of oil(s);
  b) 0.05 to 5% by weight of polymer(s) from the group including
    i. copolymers of ethylene/propylene/styrene,
    ii. copolymers of butylene/ethylene/styrene,
    iii. copolymers of butylene/propylene/styrene
  c) 1 to 70% by weight of peroxydisulfate(s),
whereby the weight ratio of sodium peroxydisulfate in the agent to the total amount of peroxydisulfates in the agent is at least 0.2.

The ready-to-use agents are prepared immediately before application to hair by mixing the two preparations (A) and (B) and optionally a third preparation (C) and/or other preparations. In the case of ready-to-use agents that are mixed from more than two preparations to form a finished application mixture, it can be immaterial whether two preparations are mixed together first and then the third preparation is added and mixed in, or whether all preparations are brought together and then mixed. The mixing can occur by stirring in a bowl or a beaker or by shaking in a closable container.

The term "immediately" in this case is to be understood as a time period from a few seconds to an hour, preferably up to 30 minutes, particularly up to 15 minutes.

The agents of the invention are used in a method for the lightening of keratinic fibers, particularly human hair, in which the agent is applied to keratin-containing fibers, left on the fiber at a temperature from room temperature to 45° C. for a treatment time of 10 to 60 minutes, and then rinsed out again with water or washed out with a shampoo.

The treatment time for the ready-to-use lightening agent is preferably 10 to 60 minutes, particularly 15 to 50 minutes, and particularly preferably 20 to 45 minutes. During the time the agent acts on the fiber, it can be advantageous to support the lightening process by application of heat. The application of heat can occur by means of an external heat source, such as with aid of a hot air blower, as well as, especially during hair lightening on live persons, by the person's body temperature. In the last option, the sections to be lightened are typically covered with a hood. A treatment phase at room temperature is also novel. The temperature during the treatment time is preferably between 20° C. and 40° C., particularly between 25° C. and 38° C. The lightening agents produce good bleaching and lightening results even at physiologically tolerable temperatures below 45° C.

After the treatment time ends, the remaining lightening preparation is rinsed out of the hair with water or a cleaning agent. Commercial shampoos in particular can function here as cleaning agents, whereby the cleaning agent can be omitted and the rinsing process can occur with tap water particularly when the lightening agent includes a carrier with a high surfactant content.

The preferred embodiments of the first subject matter of the invention apply mutatis mutandis also to the second subject matter of the invention.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An agent for lightening keratinic fibers, including, based on its weight,
   a) 20 to 75% by weight oil(s);
   b) 0.35 to 0.75% by weight of one or more polymer(s) from the group consisting of
      iv. copolymers of ethylene/propylene/styrene,
      v. copolymers of butylene/ethylene/styrene, and
      vi. copolymers of butylene/propylene/styrene; and
   c) 1 to 70% by weight of peroxydisulfate(s) comprising sodium peroxydisulfate, wherein the weight ratio of sodium peroxydisulfate in the agent to the total amount of peroxydisulfates in the agent is at least 0.2, and any ammonium peroxydisulfate present in the agent is at a concentration of 0 to 0.1% by weight, and
   wherein the agent is a foam composition.

2. The agent according to claim 1, wherein the oil(s) are at a concentration of 22.5 to 70% by weight and are selected from the group consisting of paraffin oil, polyisobutene, alkyl benzoates, isopropyl palmitate, isohexadecane, isododecane, and isononyl-isononanoate.

3. The agent according to claim 2, wherein the paraffin oil is at a concentration of 20 to 60% by weight.

4. The agent according to claim 1, comprising 0.1 to 4% by weight copolymers of ethylene/propylene/styrene.

5. The agent according to claim 1, comprising 10 to 20% by weight sodium peroxydisulfate as the peroxydisulfate(s).

6. The agent according to claim 1, comprising 5 to 40% by weight potassium peroxydisulfate as the peroxydisulfate(s).

7. The agent according to claim 5, wherein the weight ratio of sodium peroxydisulfate present in the agent to the total amount of peroxydisulfates present in the agent is 0.2 to 0.5.

8. The agent according to claim 1, further comprising 0.1 to 5% by weight xanthan.

9. The agent according to claim 1, further comprising 1 to 15% by weight cetearyl alcohol.

10. The agent according to claim 1, further comprising one or more long-chain fatty alcohols from the group consisting of arachidyl alcohol (eicosan-1-ol), gadoleyl alcohol ((9Z)-eicos-9-en-1-ol), arachidonyl alcohol ((5Z,8Z,11Z,14Z)-eicosa-5,8,11,14-tetraen-1-ol), heneicosyl alcohol (heneicosan-1-ol), behenyl alcohol (docosan-1-ol), erucyl alcohol ((13Z)-docos-13-en-1-ol), and brassidyl alcohol ((13E)-docosen-1-ol) in a total amount of 0.3 to 3.4% by weight.

11. The agent according to claim 1, further comprising, based on the total weight of the agent, 2 to 10% by weight longer-chain alcohols with a chain length of 12 to 18 C atoms.

12. The agent according to claim 1, further comprising, based on total weight of the agent, 5 to <10% by weight alkali metal metasilicates.

13. A method for changing the color of keratinic fibers, in which at least two preparations (A) and (B), packaged separate from one another, of which preparation (A) comprises at least one persulfate and preparation (B) at least one oxidizing agent, comprises:
   mixing preparations (A) and (B) to form a foamed application mixture, and applying the foamed application mixture to the fibers and rinsing the preparation out again after a treatment time,
   wherein preparation (A) comprises
      a) 20 to 75% by weight of oil(s);
      b) 0.35 to 0.75% by weight of one or more polymer(s) from the group consisting of:
         i. copolymers of ethylene/propylene/styrene,
         ii. copolymers of butylene/ethylene/styrene, and
         iii. copolymers of butylene/propylene/styrene; and
      c) 1 to 70% by weight of peroxydisulfate(s) comprising sodium peroxydisulfate, wherein any ammonium peroxydisulfate present in the agent is at a concentration of 0 to 0.1% by weight,
   wherein the weight ratio of sodium peroxydisulfate in the agent to the total amount of peroxydisulfates in the agent is at least 0.2.

* * * * *